(12) United States Patent
Bignozzi et al.

(10) Patent No.: US 8,158,137 B2
(45) Date of Patent: *Apr. 17, 2012

(54) FUNCTIONAL NANOMATERIALS WITH ANTIBACTERIAL AND ANTIVIRAL ACTIVITY

(75) Inventors: Carlo Alberto Bignozzi, London (GB); Valeria Dissette, London (GB); Alfredo Corallini, London (GB); Giacomo Carra', London (GB); Renato Della Valle, London (GB)

(73) Assignee: NM Tech Nanomaterials and Microdevices Technology Limited, London (GB)

( * ) Notice: Subject to any disclaimer, the term of this patent is extended or adjusted under 35 U.S.C. 154(b) by 996 days.

This patent is subject to a terminal disclaimer.

(21) Appl. No.: 12/093,671

(22) PCT Filed: Apr. 24, 2006

(86) PCT No.: PCT/IT2006/000280
§ 371 (c)(1),
(2), (4) Date: May 14, 2008

(87) PCT Pub. No.: WO2007/122651
PCT Pub. Date: Nov. 1, 2007

(65) Prior Publication Data
US 2008/0269186 A1    Oct. 30, 2008

(51) Int. Cl.
*A61K 8/02* (2006.01)
*A61K 31/28* (2006.01)
*A61K 31/095* (2006.01)
*A01N 55/02* (2006.01)
*A01N 65/00* (2009.01)
*A01N 31/00* (2006.01)
*A01N 25/34* (2006.01)

(52) U.S. Cl. .......... 424/401; 424/404; 514/492; 514/66; 514/706; 514/495

(58) Field of Classification Search ................ 424/401, 424/422, 423, 404; 514/492, 66, 706, 495
See application file for complete search history.

(56) References Cited

U.S. PATENT DOCUMENTS

| | | | | |
|---|---|---|---|---|
| 4,906,466 A * | 3/1990 | Edwards et al. | | 424/421 |
| 5,220,000 A | 6/1993 | Theodoropulos | | |
| 5,695,747 A * | 12/1997 | Forestier et al. | | 424/59 |
| 6,468,512 B1 * | 10/2002 | Carmody | | 424/65 |
| 7,906,132 B2 | 3/2011 | Ziegler et al. | | |
| 2004/0117007 A1 | 6/2004 | Whitbourne | | |
| 2005/0084464 A1 | 4/2005 | McGrath et al. | | |
| 2005/0112376 A1 | 5/2005 | Naasani | | |
| 2005/0175649 A1 * | 8/2005 | Disalvo et al. | | 424/401 |
| 2005/0249760 A1 | 11/2005 | Shin-Ching et al. | | |
| 2005/0265935 A1 | 12/2005 | Hollingsworth et al. | | |
| 2006/0141015 A1 * | 6/2006 | Tessier et al. | | 424/443 |
| 2008/0269186 A1 | 10/2008 | Bignozzi et al. | | |
| 2009/0270997 A1 * | 10/2009 | Bignozzi et al. | | 623/23.6 |
| 2010/0086605 A1 * | 4/2010 | Bignozzi et al. | | 424/489 |

FOREIGN PATENT DOCUMENTS

| | | |
|---|---|---|
| DE | 103 42 258 A1 | 4/2005 |
| EP | 0 279 307 A2 | 8/1988 |
| EP | 0 937 398 A1 | 8/1999 |
| WO | WO 02/085385 A2 | 10/2002 |
| WO | WO 2004/026346 A2 | 4/2004 |
| WO | WO 2005/042040 A1 | 5/2005 |
| WO | WO 2005/042041 A1 | 5/2005 |
| WO | WO 2006015317 A2 * | 2/2006 |
| WO | WO 2006/043166 A2 | 4/2006 |
| WO | WO 2006/043168 A2 | 4/2006 |
| WO | WO 2006/049379 A1 | 5/2006 |

OTHER PUBLICATIONS

Pham, et al., "Preparation and Characterization of Gold Nanoshells Coated with Self-Assembled Monolayers" Langmuir vol. 18, pp. 4915-4920, 2002.

Nazeeruddin et al., "Conversion of Light to Electricity by cis-X2Bis(2,2'-bipyridyl-4,4'-dicarboxylate)ruthenium(II) Charge-Transfer Sensitizers (X—Cl-, Br-, I-, CN-, and SCN-) on Nanocrystalline TiO2 Electrodes" J. Am. Chem. Soc., vol. 115, No. 14, pp. 6382-6390, 1993.

* cited by examiner

*Primary Examiner* — Johann Richter
*Assistant Examiner* — Abigail Fisher
(74) *Attorney, Agent, or Firm* — Dickstein Shapiro LLP

(57) ABSTRACT

The present invention relates to nanomaterials comprised of metal oxides associated with cationic metals having antibacterial activity. In particular, the present invention relates to nanocrystalline compounds of formula (I): $AO_x$-(L-Men+) i, (I) where $AO_x$ represents the metal oxide or metalloid oxide, with x=1 or 2; Me1"1" is a metal ion having antibacterial activity, with n=1 or 2; L is a bifunctional molecule, either organic or organometallic, capable of binding simultaneously with the metal oxide or metalloid oxide and the metal ion Men+; and i represents the number of L-Men+groups bound to a $AO_x$ nanoparticle.

26 Claims, 2 Drawing Sheets

FUNCTIONAL NANOMATERIALS WITH ANTIBACTERIAL AND ANTIVIRAL ACTIVITY

FIELD OF APPLICATION OF THE INVENTION

The present invention relates to nanomaterials comprised of metal oxides associated with cationic metals having antibacterial activity.

STATE OF THE ART

The antibacterial activity of certain metal ions, also called "the oligodynamic effect", is known.

The metal ions which have the greatest antibacterial activity are, in decreasing order of potency, ions of the following metals:

Hg>Ag>Cu>Zn>Fe>Pb>Bi

The incorporation of such metals, particularly silver ions, in plastic, ceramic and fiber- or carbon-based materials, enables elimination or reduction of the growth of bacterial colonies. This effect is particularly advantageous in light of the compatibility of $Ag^+$ with the human organism and the increasing resistance of many bacteria to antibiotics. Thus, the use of materials which contain silver can serve to avoid or limit bacterial proliferation.

Concerning the mechanism of action of silver, it is known that the antibacterial activity is performed by the univalent positive ion, $Ag^+$. It has been observed that the presence of platinum in mixtures with silver promotes the oxidation of Ag to $Ag^+$, due to the galvanic effect; this results in a corresponding enhancement of the antibacterial activity of the film consisting of platinum and silver. Furthermore, pharmaceuticals based on silver, e.g. silver sulfadiazine, used to prevent infections in cases of severe burns, function with slow release of $Ag^+$ ions, which can be reversibly absorbed in bacterial cells, by association with the —SH groups of cysteine in bacterial proteins present in the cell wall. The cytotoxic action of $Ag^+$ is also associated with the capability of this ion to displace essential ions from the cells, such as calcium ($Ca^{2+}$) and zinc ($Zn^{2+}$). Prior studies (see, e.g., Carr, H. S., Wlodkowski, T. J., and Rosenkranz, H. S., 1973, "Antimicrobial agents and chemotherapy", vol. 4, p. 585) have demonstrated that the antibacterial activity of $Ag^+$ ions is directly proportional to their concentration, and is effective against a very large number of species of bacteria. Similar considerations can be done for cupric ions ($Cu^{2+}$), which are known in agriculture as antibacterial agents.

As to the current state of the art, it is known to produce nanocrystalline materials with high surface area, based on metal oxides ($MO_x$), such as titanium dioxide, zinc oxide, stannic oxide (SnO2), zirconium dioxide, and colloidal silica, which can be deposited on and stably adhered to a variety of substrates. Also known are nanomaterials based on titanium dioxide which include silver ions, which are obtained by mixing suspensions of the nanomaterial with solutions containing $Ag^+$ ions. The adhesion of the $Ag^+$ ions to the nanocrystalline structure of the metal oxide is very likely associated with insertion of the ions among the nanocrystals.

In order to fabricate homogeneous films, which exhibit an effective antibacterial action, however, it is necessary to use interactions which propagate in a uniform manner over the surface of the nanomaterial and which allow the homogeneous deposition of a high concentration of silver ions.

This problem is solved by the present invention, whereby, further, films can be produced which can be deposited onto various materials and onto filters employed for purification of ambient air.

SUMMARY OF THE INVENTION

The present invention relates to the preparation of novel antibacterial and antiviral nanomaterials based on metal oxides or metalloid oxides, such as, e.g., $TiO_2$, $ZrO_2$, $SnO_2$, ZnO, and $SiO_2$, functionalized with molecular species of an organic or organometallic nature capable of binding simultaneously to the oxide and to ions of transition metals, such as $Ag^+$ or $Cu^{2+}$.

For illustrative purposes, the constituent units of these new materials may be exemplified by formula (I):

$$AO_x\text{-}(L\text{-}Me^{n+})_i \qquad (I)$$

where
$AO_x$ represents the metal oxide or metalloid oxide, with x=1 or 2;
$Me^{n+}$ is a metal ion having antibacterial activity, with n=1 or 2, preferably $Ag^+$ or $Cu^{++}$;
L is a bifunctional molecule, either organic or organometallic, capable of binding simultaneously with the metal oxide or metalloid oxide and the metal ion $Me^{n+}$; and
i represents the number of $L\text{-}Me^{n+}$ groups bound to a $AO_x$ nanoparticle.

The metal oxides or metalloid oxides $AO_x$ for use in the present invention are, for example, colloidal silica, titanium dioxide, zirconium dioxide, stannic oxide, and zinc oxide. They are insulating or semiconducting materials which are capable of adhering, either per se, or with the application of a suitable primer, to a large number of materials, including: wood, plastic, glass, metals, ceramics, cement, and internal and external building surfaces, and can be produced with the dimensions of nanoparticles on the order of nanometers. These nanomaterials are capable of adsorbing, by electrostatic or chemical interaction, such as via esteric bonds, to molecules having suitable functional groups, such as the following groups: carboxyl (—COOH) (or carboxylate), phosphonic (—$PO_3H_2$) (or phosphonate), or boronic (—$B(OH)_2$) (or boronate), with which groups the bifunctional molecules L may be provided. In view of the small dimensions of the ligands L and of the metal ions $Me^{n+}$, e.g. ions of silver or copper, which may be on the order of picometers, the result is that each nanoparticle of metal oxide can be homogeneously covered by metal ions such as $Ag^+$ or $Cu^{2+}$, as illustrated schematically by way of example in FIG. 1.

As a result, these nanomaterials, comprised of positively charged nanoparticles, can give rise to suspensions which are stable and transparent, either in aqueous solvents or in polar solvents of an organic nature.

Another significant aspect is connected with the possibility of mixing suspensions of the inventive nanomaterials with cationic surfactants, such as alkylammonium salts. In this way, the bactericidal activity of the inventive nanomaterials can be enhanced by the presence of the alkylammonium salt. Indeed, surfactants of this type display a bactericidal activity which can be complementary to that of the antibacterially active metal ions. Surprisingly, we have found that alkylammonium salts, e.g. benzalkonium chloride, which tend to precipitate in a basic medium or in the presence of high concentrations of anions, are stable in the presence of suspensions formed from the positively charged nanoparticles according to the present invention.

Experimental evidence, described hereinbelow, further indicates that cationic surfactants such as benzalkonium chloride can give rise to adsorption onto nanomaterials based on titanium dioxide under pH conditions close to neutral. This affords the further advantage of reducing the volatility of the alkylammonium salts after they have been applied to a surface.

Because of the broad spectrum of antibacterial action of materials containing silver and copper ions, the use of such materials as coatings for building interiors, bathrooms, kitchens, elements of furniture and fixtures in general, glass surfaces (such as glass doors and windows), and operating rooms, and for filters used for purifying air in various environments, as well as for water filters, unquestionably represents an area of applications of substantial importance. The production of filters made of ceramic, glass, or cellulose materials and containing silver ions or copper ions, and the introduction of said materials in conditioning plants or in forced air recycling apparatuses, enables prevention of a large number of illnesses.

The designing of such filters requires that the materials with which the filters are coated allow a high flow speed of the air, and that the bactericidal activity can be achieved under conditions of short contact times.

This problem is solved by the inventive nanomaterials, in that they cause appreciable increase in the surface area, with factors of surface area increase on the order of $10^3$, and they are capable of realizing the bactericidal action at contact times on the order of 5 minutes, as provided in the standards UNI-EN 1276 of April 2000 and UNI-EN 13697 of December 2001.

Filters coated with the inventive nanomaterials can also be easily restored to their initial antibacterial effectiveness by immersion in alcoholic solutions based on metal ions such as $Ag^+$ or $Cu^{2+}$.

DETAILED DESCRIPTION OF THE INVENTION

Figure 1:
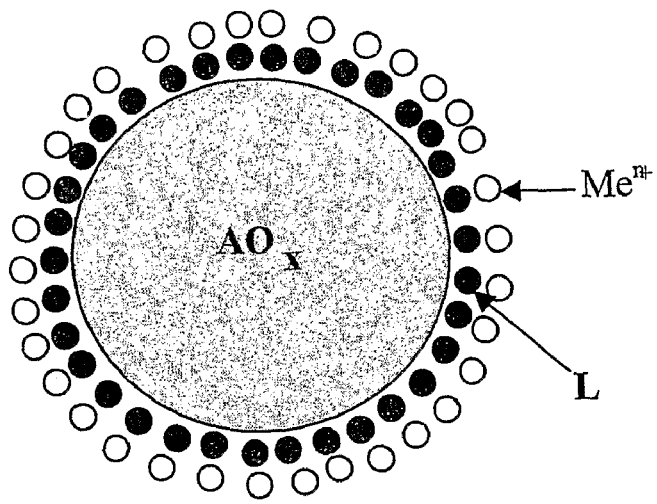
FIG. 1 illustrates schematically the structure of an inventive nanoparticle.

According to a feature of the present invention, nanocrystalline substrates comprising $AO_x$ are prepared which are modified with bifunctional ligands L comprised of organic molecules containing functional groups capable of bonding to the organic molecule to the nanocrystalline substrate, as well as functional groups capable of bonding to metal ions which have antibacterial activity, e.g. $Ag^+$ and $Cu^{2+}$ ions.

According to a second feature of the present invention, nanocrystalline substrates comprising $AO_x$ are prepared which are modified with bifunctional ligands L comprised of organometallic molecules, such as complexes of transition metals, which molecules contain functional groups capable of bonding the complex to the nanocrystalline substrate, as well as functional groups capable of bonding to metal ions which have antibacterial activity, e.g. $Ag^+$ and $Cu^{2+}$ ions.

These nanocrystalline compounds are represented by formula (I):

$$AO_x\text{-}(L\text{-}Me^{n+})_i \qquad (I)$$

where
$AO_x$ represents the metal oxide or metalloid oxide, with $x=1$ or 2;

$Me^{n+}$ is a metal ion having antibacterial activity, with $n=1$ or 2, preferably $Ag^+$ or $Cu^{++}$;

L is a bifunctional molecule, either organic or organometallic, capable of binding simultaneously with the metal oxide or metalloid oxide and the metal ion $Me^{n+}$; and i represents the number of $L\text{-}Me^{n+}$ groups bound to a $AO_x$ nanoparticle.

The value of the parameter i will depend on various factors, such as the size of the nanoparticle of $AO_x$, the nature of the ligand L, and the method used for preparing it. In the context of the present invention, i corresponds to the number of ligands L which the nanoparticle $AO_x$ is capable of bonding to when said nanoparticle is contacted with a solution of the ligand L for a time in the range of 10 min to 72 hr, preferably in the range 3 to 24 hr.

The inventive nanomaterials have particle size less than 40 nm, preferably less than 30 nm, more preferably less than 15 nm. Nanoparticles of size less than 15 nm generally give rise to transparent suspensions which have a relatively wide range of applications.

The metal oxides or metalloid oxides $AO_x$ which may be used according to the invention are, e.g.: colloidal silica, titanium dioxide, zirconium dioxide, stannic dioxide, and zinc oxide.

According to a general feature of the present invention, the antibacterial and antiviral activity of the described nanomaterials is expressed even in the absence of light irradiation.

According to a further feature of the present invention, nanocrystalline materials according to the invention, or nanocrystalline materials comprised only of $AO_x$ oxide, are mixed with cationic surfactants having antibacterial activity which are capable of being adsorbed on the surface of the nanoparticles of $AO_x$ or which are capable of giving rise to mixtures which are stable over time, which mixtures comprise suspensions of the described nanomaterials.

According to yet another feature of the present invention, one can restore the initial bactericidal activity of the substrates, in the event of depletion of the antibacterial metal ions ($Ag^+$ or $Cu^{2+}$), to its initial value, merely by immersion of the substrates in an alcoholic solution containing the specific metal ion(s).

According to another feature of the present invention, dermatologic compositions for treatment of bacterially mediated dermatologic disorders, e.g. acne and decubitus ulcers, are provided.

Bifunctional Ligands L Based on Complexes of Transition Metals

The transition metal complexes which may be used for the described purpose must contain organic ligands coordinated at a metal center, with one of the following functionalities: boronic ($—B(OH)_2$), phosphonyl ($—PO_3H_2$), or carboxyl ($—COOH$). These functionalities serve to bond the complex to the nanocrystalline substrate $AO_x$. The other groups which coordinate at the metal center are capable of bonding to metal ions with antibacterial activity. Examples of these groups are ligands of the type of: $Cl^-$, $Br^-$, $I^-$, $CNS^-$, $NH_2$, $CN^-$ and $NCS^-$.

The organometallic complexes L according to the invention preferably comprise organic ligands of the type of dipyridyl and/or terpyridyl, coordinated at a metallic center (M) and functionalized with the following groups: carboxyl (—COOH), phosphonic (—PO$_3$H$_2$), or boronic (—B(OH)$_2$), capable of bonding to nanomaterials comprised of AO$_x$; and further functionalized with the following groups: Cl$^-$, Br$^-$, I$^-$, CNS$^-$, NH$_2$, CN$^-$ or NCS$^-$, which are coordinated at said metallic center (M) and are capable of bonding to Ag$^+$ or Cu$^{2+}$, ions. Preferably, said dipyridylic or terpyridylic groups are substituted with carboxyl groups, more preferably in the para position with respect to the pyridine nitrogen. In a case in which more than one dipyridylic group or terpyridylic group is present in said organometallic complex L, optionally one of these groups may be unsubstituted.

Concerning the metal ions (M) present in L, having coordinations of the octahedral type or having other types of coordination corresponding to tetrahedral geometry, rectangular planar or square planar geometry, bipyramidal trigonal geometry, or pyramidal geometry with a square or rectangular base, candidates are any of the metals which are in the first, second, or third row of transition metals in the periodic table of the elements and which can give rise to stable bifunctional molecules of the type described.

More preferably, the described organometallic complexes L have a coordination of the octahedral type. Preferably, the transition metals coordinated by these complexes are selected from: Cr, Mn, Fe, Co, Ni, Cu, Zn, Ru, Rh, Pd, Re, Os, Ir, and Pt.

The inventive organometallic complexes L may alternatively have a negative charge, and may form salts with cations, preferably organic cations such as tetraalkylammonium cations. Such cations enable solubilization of these species in organic solvents, which contribute to the process of adsorption of the nanomaterials based on metal oxides or metalloid oxides.

Thus, these molecules can serve as bifunctional ligands capable of giving rise to a uniformly adsorbed layer on the AO$_x$ nanoparticles and at the same time can bind to metal ions with antibacterial activity.

Examples of such complexes which have octahedral coordination are presented hereinbelow.

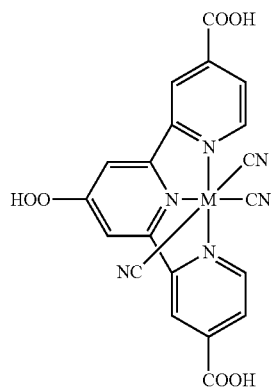

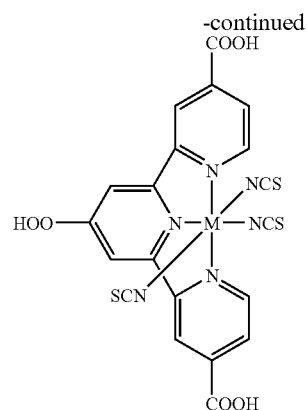

[(H$_3$Tcterpy)M(CN)$_3$]TBA [(H$_3$Tcterpy)M(NCS)$_3$]TBA
TBA=tetrabutylammonium cation.
H$_3$Tcterpy=4,4',4"-tricarboxyterpyridyl.

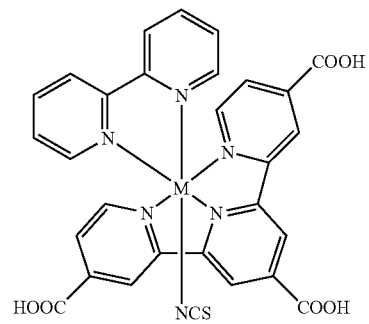

bpy=2,2'-dipyridyl.
[M(H$_3$tcterpy)(bpy)NCS]TBA
The TBA group may be replaced by other alkylammonium cations which enable solubilization of the complex in organic solvents.

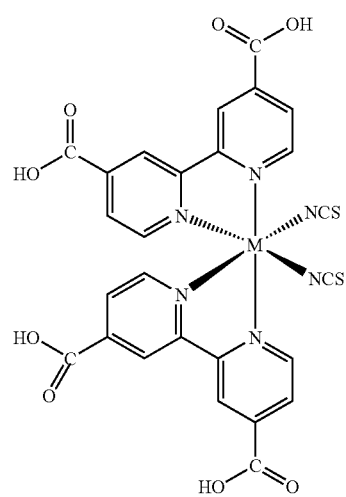

[M(H$_2$dcb)$_2$(NCS)$_2$
H$_2$dcb=2,2'-dipyridyl-4,4'-dicarboxylic acid.
Bifunctional Ligands L Based on Organic Compounds.
The bifunctional ligands L of an organic types which are usable in the context of the present invention include molecular species containing groups which can give rise to an interaction with $AO_x$ nanoparticles, and further contain functionalities which can bond to ions having antibacterial activity. Examples of such molecular species include organic molecules containing: the functional groups carboxyl (—COOH), phosphonic (—PO3H2), and boronic (—B(OH)2) which are capable of contributing to the adsorption onto the surface of the oxide $AO_x$; and the functional groups >N, >NH$_2$, —CN, —NCS, or —SH which are capable of bonding to metal ions with antibacterial activity such as $Ag^+$ or $Cu^{2+}$.

These organic ligands are preferably selected from:

nitrogen-containing heterocycles having 6 to 18 members, preferably pyridine, dipyridyl, or terpyridyl, substituted with one or more substituents selected from: carboxyl (—COOH), boronic (—B(OH)$_2$), phosphonic (—PO3H2), mercaptan (—SH), and hydroxyl (—OH);

$C_6$ to $C_{18}$ aryls, preferably selected from: phenyl, naphthyl, and biphenyl, substituted with one or more substituents selected from: carboxyl (—COOH), boronic (—B(OH)$_2$), phosphonic (—PO$_3$H2), mercaptan (—SH), and hydroxyl (—OH); and C2 to C18 monocarboxylic and dicarboxylic acids, substituted with one or more mercaptan groups (—SH) and/or hydroxyl groups (—OH).

More preferably, examples of these bifunctional organic ligands include:

pyridine, dipyridyl, or terpyridyl, functionalized with carboxyl groups, boronic groups, or phosphonic groups; mercaptosuccinic acid, mercaptoundecanoic acid, mercaptophenol, mercaptonicotinic acid, 5-carboxypentanethiol, mercaptobutyric acid, and 4-mercaptophenylboronic acid.

Experimental Methods:

The experimental methods relating to preparation of nanomaterials comprised of $AO_x$ which nanomaterials were used in the development of the present invention, the characteristics of said nanomaterials, and the antibacterial properties of said nanomaterials, will now be described.

Preparation of Transparent Suspensions of Nanomaterials Based on Titanium Dioxide and Zirconium Dioxide The nanomaterials based on titanium dioxide can be produced with nanoparticle dimensions such that they give rise to transparent or opaque suspensions in aqueous or organic solvents. Suspensions of $TiO_2$ comprised of nanoparticles of dimensions less than 15 nanometers are ordinarily transparent, and when applied to a surface they do not alter its color. Commercial titanium dioxide products such as "Biossido di Titanio P 25" (supplied by Degussa) give rise to suspensions which are white and opaque, because the mean diameter of the $TiO_2$ nanoparticles is in the range 25 to 30 nm. Either opaque or transparent nanomaterials may be used for the purposes of the present invention. However, transparent nanomaterials are of greater interest because they offer a wider range of possible applications. Transparent colloidal suspensions based on colloidal silica or stannic dioxide are commercially available.

Methods of preparing suspensions based on titanium dioxide and zirconium dioxide will be described hereinbelow. The quantities of reagents indicated may be varied without departing from the novelty and scope of the present invention.

(A) Transparent Suspensions Based on $TiO_2$:

Into a beaker there were charged 300 mL distilled $H_2O$ and 2.1 mL of a strong acid, e.g. concentrated HNO$_3$ (65% w/w). Over a period of 10 min, 50 mL titanium isopropoxide (supplied by Fluka) was added under stirring, by means of a dropping funnel. Immediately a white milky precipitate of $TiO_2$ was formed. The mixture was then heated at 80° C. for 8 to 12 hours, taking care to maintain the stirring and the temperature constant. During the heating, the precipitate redissolved, and the mixture took on an opalescent appearance. During the phase of heating, the colloidal suspension was allowed to concentrate to a final volume of 100 to 200 mL, corresponding to a $TiO_2$ concentration of 150-75 g/L. The nanoparticles of titanium dioxide obtained at the end of the process had a diameter in the range 6 to 15 nm. The suspension concentrated to 100 mL was then diluted by addition of distilled water and ethanol, to give a final transparent solution (pH≈2) which contained, in a volume of 1 liter, a concentration of $TiO_2$ of 1.5% and a percentage of alcohol in the range of 10 to 50%, preferably 25%.

(B) Transparent Suspensions Based on $ZrO_2$:

Into a beaker there were charged 300 mL distilled $H_2O$ and 2.1 mL of a strong acid, e.g. concentrated HNO$_3$ (65%). Over a period of c. 10 min, 76 mL zirconium tetraisopropoxide (70% in isopropanol) was added under stirring, by means of a dropping funnel.

A white milky precipitation of $ZrO_2$ was seen to form immediately. The mixture was then heated at 90° C. for 8 to 12 hours, taking care to maintain the stirring and to maintain constant temperature. During the heating, the precipitate redissolved, giving rise to a milky-appearing suspension, which was allowed to concentrate to 140-280 mL, corresponding to a $ZrO_2$ concentration of 150-75 g/L. The suspension concentrated to 140 mL was diluted with distilled water and ethanol to obtain 1.4 L of an opalescent suspension (pH≈2) which contained a concentration of $ZrO_2$ of 1.5% and a percentage of alcohol in the range of 10-50%, preferably 25%.

(C) Opaque Suspensions Based on $TiO_2$:

Neutral aqueous opaque suspensions based on titanium dioxide can be obtained by adding titanium dioxide P 25 to aqueous solutions of "Triton X 100" (supplied by Fluka).

Neutral aqueous opalescent suspensions based on titanium dioxide may also be prepared from peroxytitanic acid by a modification of a procedure reported in the literature (Ichinose, H., Terasaki, M., and Katsuki, H., 1996 *J. Ceramic Soc. Japan*, 104, 715).

In a typical preparation, 150 mL TiCl$_4$ in 20% HCl is charged to a 1 L beaker, and 826 mL NH$_4$OH diluted 1:9 with distilled water is added to this solution. The pH of the resulting solution is neutral (pH=7), and titanic acid, Ti(OH)$_4$, is precipitated out. This precipitate is white and has the consistency of a gel. The precipitate is collected on a filter of porosity G3, and is washed with 750-1000 mL distilled water (until complete elimination of the chloride is achieved, as can be demonstrated by treating the liquid filtrate with AgNO$_3$). If chloride is present, one notices the precipitation of white caseous AgCl. The precipitate comprised of titanic acid, Ti(OH)$_4$, is collected and is suspended in 200 mL distilled water having conductivity less than 1.5 μS and having pH in the interval 5-7; to this there is added slowly over a period of 20-30 minutes 92 mL of 30% $H_2O_2$— The dissolution of the precipitate is noted, and the formation of a yellow-colored solution containing peroxytitanic acid, of general formula

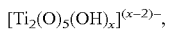

where x is in the range 3-6.

Finally the solution is heated 1 hr at 70° C. to decompose the excess $H_2O_2$, and is then autoclaved 8 hr at 120° C. In this phase of the procedure, the peroxytitanic acid decomposes to titanium dioxide, principally in the allotropic form of anatase. The resulting suspension of nanoparticles has a pH close to neutral, and an opaque appearance, and is stable over time.

Production of Suspensions of Nanomaterials having Antibacterial and Antiviral Activity To confer bactericidal activity and antiviral activity on the suspensions of nanomaterials, a first stage of adsorption is carried out wherein the bifunctional ligand L is adsorbed, followed by mixing with an aqueous or alcoholic solution containing $Ag^+$ or $Cu^{2+}$ ions. The ammonium salt acting as the cationic surfactant, which has antibacterial activity, may then be added to the suspension of nanomaterials functionalized with $Ag^+$ or $Cu^{2+}$, ions, or may be independently added to or adsorbed onto the nanomaterials which are the subjects of the present invention; these preparations have been described above.

In general, adsorption of the bifunctional ligand L onto a nanomaterial $AO_x$ described in the present invention requires times on the order of 12-36 hr, whereas the bonding of $Ag^+$ or $Cu^{2+}$ ions to the ligand L is stabilized nearly instantly by addition of solutions containing these ions to the suspensions of the nanomaterials functionalized with the ligand L. The experimental evidence accumulated, described hereinbelow, indicates that the cationic surfactants as well, such as alkylammonium salts, may also be partially adsorbed on the surface of the nanomaterials.

The preparation methods described below demonstrate in detail the preparative methodology for providing the suspensions of nanomaterials with bifunctional ligands L, with $Ag^+$ ions, and with cationic surfactants. Analogous preparation methods may be used to provide such suspensions with $Cu^{2+}$ ions. The amounts of reagents indicated may be varied within the scope of the present invention.

(D) Adsorption of 4-mercaptophenylboronic Acid and $Ag^+$ Ions onto "$TiO_2$ P25" (Supplied by Degussa)

Figure 2:
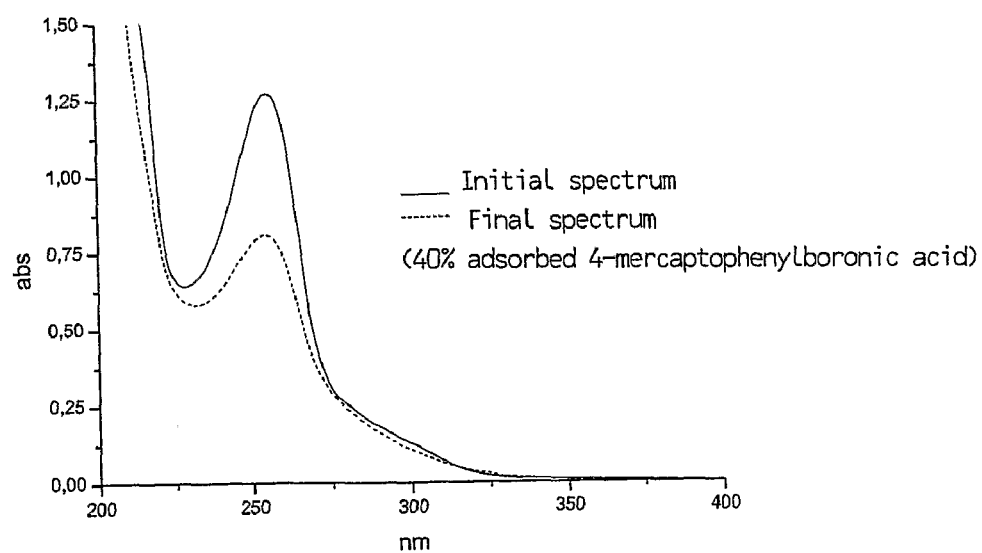
FIG. 2 illustrates an electronic absorption spectrum indicating the degree of adsorption of 4-mercaptophenylboronic acid on $TiO_2$.

To a solution containing $2 \times 10^{-5}$ moles of 4-mercaptophenylboronic acid dissolved in 50 mL ethanol there was added 1 g of $TiO_2$ P25 (supplied by Degussa). The suspension was stirred 24 hr. 4-mercaptophenylboronic acid has an absorption band at 255 nm, attributable to the $\pi$-$\pi^*$ transition in the phenolic ring. This electronic absorption band permits one to monitor the adsorption of the boronic acid onto the surface of the nanomaterial as a function of time. It is known that the adsorption occurs by interaction of the boronic function with the surface of the semiconductor. The electronic absorption spectra in FIG. 2 demonstrate that the quantity of 4-mercaptophenylboronic acid adsorbed on the surface of the "$TiO_2$ P 25" reaches 35% of the initial concentration in 24 hr.

The solution was centrifuged 10 min at 4000 rpm, obtaining a clear solution, the solid was washed with 20 mL ethanol, and was then re-suspended with 50 mL ethanol under stirring. To this suspension was added $7.2 \times 10^{-6}$ moles of a soluble silver salt, preferably silver lactate or silver acetate. The suspension obtained was white in color, odorless, and stable over time.

(E) Adsorption of 4-mercaptophenylboronic Acid and $Ag^+$ Ions Onto Transparent Suspensions of $TiO_2$ According to Method (A), and Onto Products of the Firm NM Tech 100 mL of a transparent solution of titanium dioxide prepared according to method (A) and containing 15% $TiO_2$ was diluted with 100 mL distilled water and with 200 mL of a solution of 0.052 g 4-mercaptophenylboronic acid dissolved in ethanol. The suspension was stirred 24 hr, at the end of which period a spectrophotometric determination revealed that the boronic acid was completely adsorbed on the semiconductor nanoparticles. The small dimensions of the nanoparticles with respect to "$TiO_2$ P25" and the consequent larger surface area of the suspended matter are responsible for the complete adsorption of the bifunctional ligand. To the transparent odorless suspension there was added under stirring a stoichiometric amount (with respect to L) of a silver salt, e.g., silver lactate (0.06 g) or silver acetate (0.05 g). After 1 hr of continuous stirring, there was added 10-20 mL, preferably 12 mL, of a 50% (w/v) aqueous solution of benzalkonium chloride, and the suspension was stirred for an additional 1 hr. The concentrated suspension was then diluted with distilled water and ethanol to obtain 1 L of an opalescent suspension (pH≈2) which contained $TiO_2$ in a concentration of 1.5% and ethanol in the range 10-50%, preferably 25%.

The transparent suspension was found to be indefinitely stable. Hereinbelow, this product will be designated "Bactercline", for the sake of brevity.

The same procedure may be employed to modify transparent suspensions of nanomaterials marketed by NM Tech Ltd. and designated "PSO 419", wherewith the amounts of bifunctional ligand and of silver ions are adjusted based on the amount of titanium dioxide in the product. For example, the product "PSO-419 D2" which is similar to the product prepared according to method (A), and which has a content of $TiO_2$ of 2% and pH c. 2, can be converted into an antibacterial and antiviral product using a method analogous to that described above.

In particular, 50 mL of "PSO-419D2" solution containing 2% $TiO_2$ is diluted with 2.2 mg 4-mercaptophenylboronic acid ($2.05 \times 10^{-5}$ M), and the suspension is stirred 24 hr. To the resulting odorless solution there is added $2.05 \times 10^{-5}$ M silver lactate or silver acetate. Finally, after 1 hr of continuous stirring, 8-20 mL, preferably 12 mL of an aqueous solution of dimethyl benzyl dodecyl ammonium chloride (50% w/v) is added, and the suspension is stirred for an additional 1 hr. The resulting transparent suspension is indefinitely stable.

It should be noted that other opaque products marketed by NM Tech Ltd., such as "AT-01" and "AT-03", based on $TiO_2$, can be treated according to the described methods according to the present invention, to give rise to stabile suspensions or powders which have antibacterial and antiviral activity. For example: A sample of 50 mL of a solution of "AT-01" containing 1.7% $TiO_2$ was diluted with 50 mL ethanol containing 3.8 mg of dissolved 4-mercaptophenylboronic acid ($1.9 \times 10^{-5}$ M), and the suspension was stirred 24 hr, yielding an odorless product. Then $1.9 \times 10^{-5}$ M silver lactate or silver acetate was added. The resulting suspension gave rise to a fine precipitate, after a period of time.

(F) Adsorption of Cationic Surfactants Onto Titanium Dioxide

Cationic surfactants with antibacterial activity are generally adsorbable onto nanomaterials based on $TiO_2$, $ZrO_2$, $SnO_2$, $ZnO$ and $SiO_2$. The adsorption occurs nearly instantaneously onto negatively charged or neutral nanoparticles. In the case of suspensions of nanomaterials with basic pH, the addition of benzalkonium-type salts, such as e.g. benzyl dodecyl dimethyl ammonium chloride or benzyl hexadecyl dimethyl ammonium chloride or benzalkonium chloride, causes precipitation of the suspension; whereas in the case of suspensions of nanomaterials with neutral or acidic pH the suspension is stable.

Indirect tests of the adsorption of benzalkonium chloride on nanomaterials based on $TiO_2$ at neutral pH employ conductimetric measurements. The association via adsorption of the benzyl dialkyl ammonium cation on the $TiO_2$ should predictably cause a reduction in conductivity, as was verified in the following experiment:

A 50% (w/v) solution of benzalkonium chloride diluted 1:10 has a conductivity of 4.7 mS. If the volume of this solution is increased by 10 to 15 mL by addition of distilled water, the conductivity is reduced to 3.90 mS. If instead one dilutes the solution by adding 5 mL of a neutral suspension of titanium dioxide prepared, according to method (C), from peroxytitanic acid, or the equivalent "AT-03" product at neutral pH, the conductivity measured is 3.60 mS. The reduction in conductivity by 300 μS is attributable to the adsorption of the cationic surfactant onto the surface of the titanium dioxide.

(G) Adsorption of 2,2'-dipyridyl-4-carboxy-4'-carboxylate acid, $Ag^+$, and $Cu^{2+}$, onto "$TiO_2$ P255" (Supplied by Degussa)

The 2-2'-dipyridyl-4-carboxy-4'-carboxylate anion acid (abbreviated "Hdcb") is produced by adding one equivalent of tetrabutylammonium hydroxide (abbreviated TBAOH) to 2,2'1-dipyridyl-4,4'dicarboxylic acid (abbreviated $H_2dcb$), which is scarcely soluble and is in solid form. The ligand in the monocarboxylate form (also called "monoprotonated form"), and as a tetrabutylammonium salt (abbreviated "TBA (Hdcb)"), can thus be solubilized in methanol or ethanol and can be adsorbed on titanium dioxide.

To a solution of $1 \times 10^{-4}$ moles TBA(Hdcb) in 100 mL ethanol there was added 5 g "$TiO_2$ P255" (supplied by Degussa). The suspension was stirred 24 hr. The ligand TBA (Hdcb) has an absorption band at 294 nm, due to $\pi$-$\pi$* transitions, which allows monitoring of its adsorption onto nanomaterials as a function of time.

Figure 3:
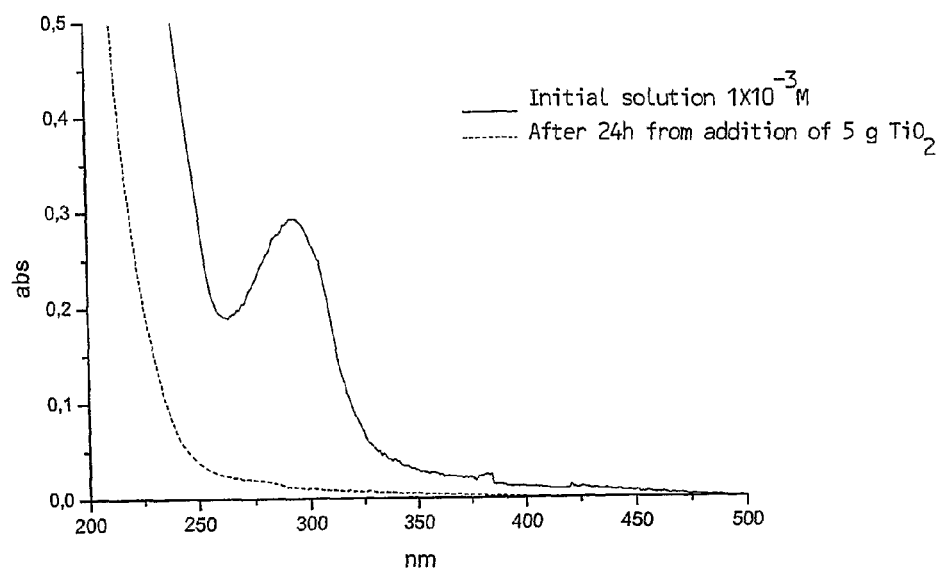
FIG. 3 illustrates an electronic absorption spectrum indicating the degree of adsorption of TBA(Hdcb) on $TiO_2$.

The spectra in FIG. 3 show that after 24 hr the ligand was completely adsorbed onto the surface of the nanocrystalline substrate. It is known that the adsorption occurs by interaction of the carboxyl functions with the surface of the semiconductor.

The suspension was then centrifuged 10 min at 4000 rpm, and the solid was washed with 50 mL methanol. The nanomaterial obtained, functionalized with the ligand (abbreviated $TiO_2$/TBA(Hdcb)), was then finally vacuum-dried at ambient temperature.

Two portions of 2 g each, of the $TiO_2$/TBA(Hdcb), were re-suspended in 100 mL ethanol. To one suspension there was added 8 mg silver lactate, under stirring; and to the other suspension there was added 7 mg $CuCl_2$. The two suspensions had different stabilities: the suspension functionalized with copper ions, $TiO_2$/TBA[Hdcb]/$Cu^{2+}$, remained stable, while that functionalized with silver ions, $TiO_2$/TBA[Hdcb]/$Ag^+$, precipitated over time.

(H) Adsorption of Organometallic Ligands (L) and $Ag^+$ Ions on Neutral Suspensions of $TiO_2$ Bifunctional organometallic ligands L as described supra can be anchored to neutral suspensions of titanium dioxide prepared according to method (C), with the nanomaterials being suspended in alcoholic solutions of concentration c. $10^{-3}$-$10^{-4}$ M of the bifunctional organometallic ligands. The suspension is stirred 12 hr, during which time the organometallic ligand L is completely adsorbed onto the surface of the nanomaterials.

Figure 4:
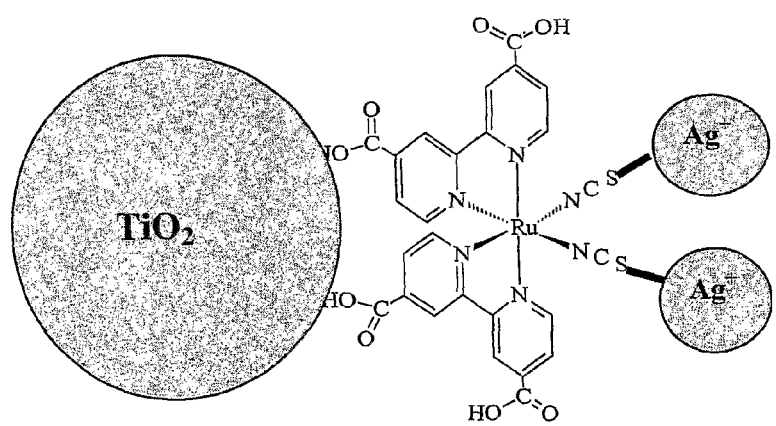
FIG. 4 is a schematic representation of a particular embodiment of an inventive nanoparticle.

The addition of stoichiometric amounts of silver with respect to the ligand L, in alcoholic solution, corresponds to formation of adducts in which the silver ion $Ag^+$ is anchored to the inorganic ligand, as illustrated schematically in FIG. 4 in the case of the complex $(H_2dcb)_2Ru(NCS)_2$ ($H_2dcb$=2,2'-dipyridyl-4,4'-dicarboxylic acid). The presence of the carboxyl functions enables adsorption of the complex, and homogeneous covering of the nanocrystalline material, in a time on the order of 2-3 hr at 50° C., and 12 hr at ambient temperature. In a subsequent step, a silver salt, e.g. silver nitrate, silver lactate, or silver acetate, is added to the methanolic solution, in a stoichiometric ratio of 2:1 with respect to the moles of $(H_2dcb)_2Ru(NCS)_2$. The presence of the two NCS groups allows the $Ag^+$ ions to be instantaneously bonded as illustrated in FIG. 4.

According to a particular embodiment of the present invention, the nanocrystalline materials according to formula (I) may be included in dermatologic compositions for treatment of bacterial dermatologic diseases, such as, e.g., acne or decubitus ulcers.

The preparation of some of such compositions is described hereinbelow, for purposes of example.

Preparation of Gels and Creams:

The suspensions of nanomaterials based on titanium dioxide, according to the invention, can be used as active ingredients in the preparation of hydrophilic gels and creams for dermatologic use. The preparation of the hydrophilic gels involves mixing of the active ingredients with excipients and jellifying agents such as, e.g. glycerin, amidopropylene glycol, magnesium silicate, and aluminum silicate. The preparation of the hydrophylic cremes involves mixing of a pharmaceutically effective quantity of the active ingredients with surfactants and emulsifiers, comprising, e.g., Vaseline, liquid paraffin, stearyl alcohol, polyethylene glycol stearate, carboxypolymethylene, and sodium edetate. Of course, any excipient approved for such uses (which excipients are well known to persons skilled in the art) may be used in preparation of the inventive dermatologic compositions.

Antibacterial and Antiviral Activity of the Functionalized Nanomaterials

The functionalized nanomaterials obtained according to the methods (D), (E), (F), (G), and (H) all had antibacterial activity against *Escherichia coli*. The testing was conducted by depositing films comprised of the various nanomaterials on Petri capsules in contact with a number of colonies greater than $10^4$ cfu (colony forming units). In all cases, complete mortality of the colonies was observed.

More thorough measurements were carried out according to the standards UNI-EN 1276 of April 2000 and UNI-EN 13697 of December 2001, for the product synthesized according to method (E) (product designated Bactercline), which product is transparent and thus applicable in a broader range of applications.

Evaluation of the Bactericidal Activity in Suspension: Method of Dilution and Neutralization (UNI-EN 1276 of April 2000):

Microorganisms

The following strains were used for the testing:

*Pseudomonas aeruginosa*
*Staphylococcus aureus*
*Staphylococcus epidermidis*
*Enterococcus faecalis*
*Escherichia coli*
*Salmonella*
*Listeria*.

Sources of the Bacteria:

All of the bacterial strains tested were provided by the Department of Experimental and Diagnostic Medicine, Microbiology Section, of the University of Ferrara.

The Bactercline product tested was diluted to 80%.

The substance being tested was deemed bactericidal if for each bacterial strain at 20° C. after a contact time of 5 min, a reduction of vitality of at least $10^5$ units ensued.

The results obtained indicate that in all cases a reduction in vitality of greater than $10^5$ units was obtained.

Conclusions:

Based on the results obtained and the validity criteria of the tests, the "Bactercline" substance tested is bactericidal against *Pseudomonas aeruginosa, Escherichia coli, Enterococcus faecalis, Staphylococcus epidermidis, Staphylococcus aureus, Salmonella,* and *Listeria,* when used at a concentration of 80% (which turns out to be the maximum testable concentration), after 5 min of contact in the presence of bovine albumin at a final concentration of 0.3%, according to the method of the standard UNI-EN 1276 of April 2000.

Evaluation of Bactericidal Activity: Surface Test (Standard UNI-EN 13697 of December 2001): Microorganisms In addition to the strains used for the test of the suspensions, supra, in the present case the testing was extended to *Legionella pneumophila*.

The list of strains employed in the tests was thus the following:

*Pseudomonas aeruginosa*
*Staphylococcus aureus*
*Staphylococcus epidermidis*
*Enterococcus faecalis*
*Escherichia coli*
*Salmonella*
*Listeria*
*Legionella pneumophila*.

The substance being tested was deemed bactericidal against the bacterial strains provided according to the European Standard if for each bacterial strain, at 20° C. after a contact time of 5 min, a reduction of vitality of at least $10^4$ units ensued.

The results obtained, reported in the Table inf ra, indicate that in all cases the decimal logarithm of the antimicrobial activity was greater than 4.

| TEST MICROORGANISMS | Contact time, and logarithm of the antimicrobial activity: 5 minutes [concentration] 100% |
|---|---|
| *Staphylococcus aureus* | >4.02 |
| *Staphylococcus epidermidis* | >4.00 |
| *Pseudomonas aeruginosa* | >4.00 |
| *Escherichia coli* | >4.00 |
| *Enterococcus faecalis* | >4.19 |
| *Salmonella* | >4.00 |
| *Listeria* | >4.00 |
| *Legionella pneumophila* | >4.26 |

Conclusions:

Based on the results obtained and the validity criteria of the tests, the "Bactercline" substance tested under the stated test conditions is bactericidal against *Pseudomonas aeruginosa, Escherichia coli, Enterococcus faecalis, Staphylococcus epidermidis, Staphylococcus aureus, Salmonella, Listeria,* and *Legionella pneumophila*, when used at a concentration of 100%, after 5 min of contact in the presence of bovine albumin at a final concentration of 0.3%, according to the method of the standard UNI-EN 13697 of December 2001.

Evaluation of the Fungicidal Activity in Suspension Method of Dilution and Neutralization (Standard UNI-EN 1650 of October 2000):

Microorganisms:
The following strains were used for the testing:
*Candida albicans*
*Aspergillus niger.*

The strains tested were provided by the Department of Experimental and Diagnostic Medicine, Microbiology Section, of the University of Ferrara.

The substance being tested was deemed fungicidal if, for each of the mycotic strains, at 20° C. after a contact time of 15 min, a reduction of vitality of at least $10^4$ units ensued.

Results
The reductions in vitality for various concentrations of "Bactercline" are presented below:

| | TIME OF CONTACT, AND REDUCTION IN VITALITY 15 minutes | | |
|---|---|---|---|
| TEST MICROORGANISMS | 25% | 50% | 80% |
| *Candida albicans* | >1.13 × 10⁴ | >1.13 × 10⁴ | >1.13 × 10⁴ |
| *Aspergillus niger* | <1.87 × 10³ | >1.37 × 10⁴ | >1.37 × 10⁴ |

Conclusions

Based on the results obtained and the validity criteria of the tests, the "Bacterclinel" substance tested is fungicidal against *Candida albicans* at concentrations of 25%, 50%, and 80%, and against *Aspergillus niger* at concentrations of 50% and 80% (which turns out to be the maximum concentration testable), after 15 min of contact in the presence of bovine albumin at a final concentration of 0.3%, according to the method of the standard UNI-EN 1650 of October 2000.

Evaluation of Fungicidal Activity: Surface Test (Standard UNI-EN 13697 of December 2001):

Microorganisms
The following strains were used for the testing:
*Candida albicans*
*Aspergillus niger.*

The strains tested were provided by the Department of Experimental and Diagnostic Medicine, Microbiology Section, of the University of Ferrara.

The substance being tested was deemed fungicidal if the logarithm of the antimicrobial activity against the microbial strains provided according to the European Standard was greater than or equal to 3, for 15 minutes of contact at 20° C.

Results
The logarithms of the reductions are presented in the following Table:

| | Contact time, and logarithm of the antimicrobial activity 15 minutes | |
|---|---|---|
| TEST MICROORGANISMS | 50% | 100% |
| *Candida albicans* | 2.02 | >3.18 |
| *Aspergillus niger* | 1.14 | >3.04 |

Conclusions

Based on the results obtained and the validity criteria of the tests, the "Bacteraline" substance tested under the stated test conditions is fungicidal against *Candida albicans* and *Aspergillus niger*, when used at a concentration of 100%, after 15 min of contact in the presence of bovine albumin at a final concentration of 0.3%, according to the method of the standard UNI-EN 13697 of December 2001.

Virucidal Activity:

The experiments described hereinbelow demonstrate that the product Bactercline, in very low concentrations, has high virucidal activity against the HSV-1 virus (herpes simplex virus-1).

Experimental Procedure

Various amounts of viral suspensions were prepared in modified Dulbecco medium (D-MEM) to which 1% of bovine fetal serum (BFS) had been added. A virus concentration (virus titer) Of $1\times10^6$ cytolytic plaque forming units (Pfu) was used. Different amounts of Bactercline were added to different samples, with pre-treatment times of 1 and 5 hr. Untreated viral suspensions were maintained as a control. After a period of incubation at ambient temperature, all of the samples were diluted to known volumes, for determining the titers of the virus. The viral titers of the controls and of the samples treated with Bactercline were determined by the method described hereinbelow.

In determining the viral titer, one calculates the number of infectious present in 1 mL of solution. One method used consists of determining the number of cytolysis plaques produced by a sufficiently diluted viral suspension and placed in contact with a monolayer of cells. In this series of experiments, renal cells of African Monkey were used (Vero). The cells were cultured at 37° C., in the presence of 5% of $CO_2$ in "D-MEM" to which 10% BFS, 1% L-glutamine, and 1% penicillin/streptomycin had been added. The determination of the titer was carried out on plates having 12 wells. When the cultures were nearly confluent, the viral stock was diluted to known concentrations in a medium containing 2% BFS. For each dilution, 2 wells on the plate were inoculated. After incubation 1 hr at 37° C., the inoculum was drawn off and the infection was blocked by adding a medium containing 1% BFS and 2% human gamma-globulin, having the function of inhibiting formation of secondary plaques.

The inoculated cultures were incubated at 37° C. for 2 days, and were monitored until the lysis plaques were visible. At this point, the cells were fixed and were stained with gentian violet. Under an optical microscope, the plaques present in the wells were counted and this count was multiplied by the dilution factor, to obtain the viral titer, in units of Pfu/mL.

Results, and Discussion

Virucidal Activity of the Bactercline Product

The Bactercline product in the amount of 10 and 50 microliters was contacted with HSV-1 having a viral titer of $1\times10^6$ Pfu. The incubation was carried out in 1 mL of D-MEM medium to which 1% of BFS had been added. Two different incubation times were used: 1 hr and 5 hr. After the given incubation period, the virus was diluted to concentrations of $1\times10^3$ and $1\times10^2$ Pfu, and the nearly confluent cultures were inoculated. As shown in Table 1, infra, the cells inoculated with the virus pretreated with Bactercline did not have lysis plaques, for either of the pretreatment times and either of the virus dilutions.

The titer of the HSV-1 virus of the controls indicated in Table 1, supra, was calculated by multiplying the mean number of cytolysis plaques times the dilution factor ($10^3$). As seen from Table 1, the treated samples experienced a reduction of 100% in cytolysis plaque formation, compared to the controls.

For both pretreatment times and both dilutions of the virus, there was nearly total reduction of the viral particles present. The product reduced the viral titer from about 300,000 viral particles present (in the control) to a titer of less than 1000. Thus, in 1 hour of contact, Bactercline diluted to 1% (10 microliter/mL) caused nearly total mortality of the viral particles.

Conclusions

This study of the antiviral activity of the Bactercline product shows that the product has antiviral activity for direct contact with HSV-1 virus even at extreme dilutions of the product, at a contact time of 1 hr.

The experiments carried out demonstrated that at a level of dilution of the product of on the order of 1:100 one achieves nearly total mortality of the viral particles.

The inventive compositions may be employed in any applications in which it is desired to achieve an antibacterial and/or antiviral effect, such as for treatment of surfaces such as surfaces in health care environments (clinics, hospitals, etc.), particularly floors, walls, tables, operating tables, etc. Another application for which the inventive compositions display advantageous activity is treatment of air in various environments, particularly in public spaces and/or health care spaces, or other environments in which it is desirable to have nearly completely sterile air, such as pharmaceutical manufacturing plants and food processing plants. In those applications, the inventive compositions may be used for coating filters employed in various types of ventilation systems, for treatment of spaces of large or small dimensions.

According to a further embodiment of the invention, dermatologic compositions are provided, for treatment of bacterial infections, which contain either along with or in replacement of the nanocrystalline materials of Formula (I): photocatalytic suspensions of $TiO_2$, in combination with silver or a derivative of silver and/or copper or a derivative of copper(II), such as described, by way of example, in Italian Patent Application Number IS2005A2 filed Sep. 1, 2005.

TABLE 1

Number of Pfu and percent of inhibition of the formation of cytolysis plaques, compared to the control, after pretreatment of HSV-1 $1 \times 10^6$ with 1 μl/mL of Bactercline. The value was calculated for dilutions of HSV-1 of $1 \times 10^3$ and $1 \times 10^2$ Pfu. Pretreatment of HSV-1 in a titer of $1 \times 10^6$ with 10 μL and 50 μL di the product being tested:
Dilution of the HSV-1 ($1 \times 10^3$ Pfu)

| Mean of the controls (Pfu) | | Mean of the samples treated with 10 μL (Pfu) | | Inhibition of plaque formation (%) | Mean of the samples treated with 50 μL (Pfu) | | Inhibition of plaque formation (%) | Viral titer of the controls | |
|---|---|---|---|---|---|---|---|---|---|
| 1 hr | 5 hr | 1 hr | 5 hr | 1 hr and 5 hr | 1 hr | 5 hr | 1 hr and 5 hr | 1 hr | 5 hr |
| 63 | 78 | | | 100 | | | 100 | $2.63 \times 10^5$ | $1.78 \times 10^5$ |

The invention claimed is:

1. Nanocrystalline compounds of formula (I):

$$AO_x\text{-}(L\text{-}Me^{n+})_i \qquad (I)$$

where $AO_x$ represents a metal oxide or metalloid oxide, with x=1 or 2;

$Me^{n+}$ is a metal ion having antibacterial activity, with n=1 or 2;

L is the bifunctional molecule 4-mercaptophenylboronic acid, which is capable of binding simultaneously with the metal oxide or metalloid oxide and the metal ion $Me^{n+}$; and i represents the number of $L\text{-}Me^{n+}$ groups bound to a $AO_x$ nanoparticle wherein $AO_x$ is functionalized with 4-mercapotophenylboronic acid and 4-mercaptophenylboronic acid binds $Me^{n+}$.

2. The nanocrystalline compounds according to claim 1, wherein $Me^{n+}$ is selected from the group consisting of $Ag^+$ and $Cu^{++}$.

3. The nanocrystalline compounds according to claim 1, wherein said metal oxides or metalloid oxides $AO_x$ are selected from the group consisting of colloidal silica, titanium dioxide, zirconium dioxide, stannic dioxide, and zinc oxide.

4. The nanocrystalline compounds according to claim 1, wherein said metal ion $Me^{n+}$ comprises an ion of a metal selected from the group consisting of Cr, Mn, Fe, Co, Ni, Cu, Zn, Ru, Rh, Pd, Re, Os, Ir, and Pt.

5. The nanocrystalline compounds according to claim 1, wherein said organometallic complexes have a geometric structure selected from the group consisting of octahedral, tetrahedral, rectangular planar, square planar, bipyramidal trigonal, pyramidal with a square base, and pyramidal with a rectangular base.

6. The nanocrystalline compounds according to claim 1, said nanocrystalline compounds having a particle size less than 40 nm.

7. The nanocrystalline compounds according to claim 1, said nanocrystalline compounds having a particle size less than 15 nm.

8. Composition comprising at least one of the nanocrystalline compounds according to claim 1, and a cationic surfactant.

9. The composition according to claim 8, wherein said cationic surfactant is an alkylammonium salt.

10. The composition according to claim 8, wherein the composition is a clear solution.

11. Nanocrystalline compounds according to claim 1, wherein at least one molecule of an alkylammonium salt is adsorbed onto the surface of said nanocrystaline compounds.

12. Dermatologic compositions comprising at least one nanocrystalline compound according to any claim 1, and further comprising one or more pharmaceutically or cosmetologically acceptable excipients.

13. The dermatologic compositions according to claim 12, said composition being in the form of a gel or cream.

14. The dermatologic compositions according to claim 13, wherein, if said composition is the form of a hydrophilic gel, then the hydrophilic gel contains at least one excipient selected from the group consisting of glycerin, amidopropylene glycol, magnesium silicate, and aluminum silicate; and if said composition is in the form of a hydrophilic cream, then the hydrophilic cream contains at least one excipient selected from the group consisting of surfactants and emulsifiers.

15. A method of making a medicament having antibacterial activity, antiviral activity, or both antibacterial and antiviral activity comprising providing at least one of the nanocrystalline compounds according to claim 1 and making a medicament that comprises said at least one of said nanocrystalline compounds.

16. A method of treating a surface with an antibacterial and/or antiviral agent comprising providing at least one of the nanocrystalline compounds according to claim 1 as an antibacterial and/or antiviral agent, and applying the nanocrystalline compounds to a surface.

17. The method of claim 16, wherein the surface is used in building interiors, elements of furniture, glass surfaces, operating rooms, or air or water purification filters.

18. A method of regeneration of nanocrystalline compounds according to claim 1, comprising a step of contacting said nanocrystalline compounds with a solution of a silver (I) salt or a solution of a copper (II) salt.

19. Dermatologic compositions comprising at least one of the nanocrystalline compounds of claim 1 and further comprising one or more pharmaceutically or cosmetologically acceptable excipients.

20. The dermatologic composition according to claim 19, wherein said one or more metal or metalloid oxides $AO_x$ are selected from the group consisting of colloidal silica, titanium dioxide, zirconium dioxide, stannic dioxide, and zinc oxide.

21. Dermatologic compositions according to claim 19, said compositions being in the form of a gel or cream.

22. The dermatologic compositions according to claim 21, wherein, if said compositions are in the form of a hydrophilic gel, the hydrophilic gel contains at least one excipient selected from the group consisting of glycerin, amidopropylene glycol, magnesium silicate, and aluminum silicate; and if said composition is in the form of a hydrophilic cream, the hydrophilic cream contains at least one excipient selected from the group consisting of surfactants and emulsifiers.

23. The composition of claim 8, wherein the cationic surfactant is selected from the group consisting of quaternary ammonium salts, chloroalkylammonium chloride, and benzalkonium chloride.

24. A composition comprising one or more nanocrystalline compounds of claim 1, wherein at least one molecule selected from the group consisting of quaternary ammonium salts, benzyl C12-C14, chloroalkylammonium chloride, and benzalkonium is absorbed on the surface of said nanocrystalline compounds.

25. The dermatologic compositions according to claim 14, wherein the surfactants and emulsifiers are selected from the group consisting of Vaseline, liquid paraffin, stearyl alcohol, polyethylene glycol stearate, carboxypolymethylene, and sodium edetate.

26. The dermatologic compositions according to claim 22, wherein the surfactants and emulsifiers are selected from the group consisting of Vaseline, liquid paraffin, stearyl alcohol, polyethylene glycol stearate, carboxypolymethylene, and sodium edetate.

* * * * *